United States Patent [19]
Peters

[11] Patent Number: 5,139,477
[45] Date of Patent: Aug. 18, 1992

[54] KNEE SLEEVE

[75] Inventor: Helena Peters, Bromma, Sweden

[73] Assignee: Camp International, Inc., Jackson, Mich.

[21] Appl. No.: 691,993

[22] Filed: Apr. 26, 1991

[51] Int. Cl.$^5$ .............................................. A61F 5/00
[52] U.S. Cl. ........................................ 602/26; 602/23; 602/62
[58] Field of Search ................... 128/80 C, 165, 87 R; 2/22, 24

[56] References Cited

U.S. PATENT DOCUMENTS

| | | |
|---|---|---|
| 3,786,804 | 1/1974 | Lewis . |
| 3,804,084 | 4/1974 | Lehman . |
| 3,831,467 | 8/1974 | Moore . |
| 3,935,858 | 2/1976 | Harroff . |
| 4,013,070 | 3/1977 | Harroff . |
| 4,084,586 | 4/1978 | Hettick . |
| 4,296,744 | 10/1981 | Palumbo ............................ 128/165 |
| 4,423,720 | 1/1984 | Meier et al. . |
| 4,724,831 | 2/1988 | Huntjens ........................... 128/80 C |
| 4,832,010 | 5/1989 | Lerman ............................. 128/80 C |
| 4,961,418 | 10/1990 | Milaurin-Smith ................... 128/165 |
| 5,024,216 | 6/1991 | Shiono ..................................... 2/24 |

Primary Examiner—Richard J. Apley
Assistant Examiner—Lynne Reichard
Attorney, Agent, or Firm—Price, Heneveld, Cooper, DeWitt & Litton

[57] ABSTRACT

There is disclosed a ready-to-wear pull-on knee support adapted to be placed over the knee, said support comprising a generally cylindrical body comprising a resilient flexible unitary sleeve, which is preferably formed from an elasticized fabric laminate. The elasticized fabric laminate includes an open-cell polymeric foam core, an outer surface comprising an elasticized fabric having a looped structure and an inner surface for wear next to the body, comprising an elasticized cotton fabric. The support includes integral parallel proximal and distal encircling straps adapted to encircle the lower thigh and upper calf, respectively, medial and lateral stabilizing or reinforcing straps and infinitely adjustable proximal and distal posterior closure means. A patella opening can be provided for patella support. A popliteal opening can be provided or the popliteal area may be covered, in which case the popliteal area is formed with a C-seam extending outwardly from the distal and proximal closure means over the outer popliteal area.

10 Claims, 4 Drawing Sheets

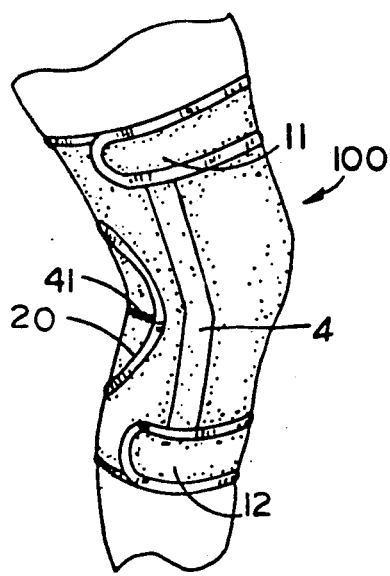
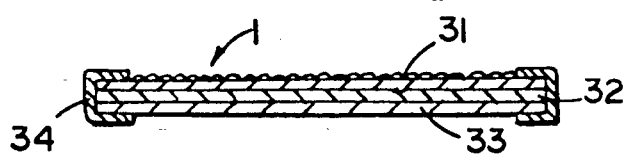
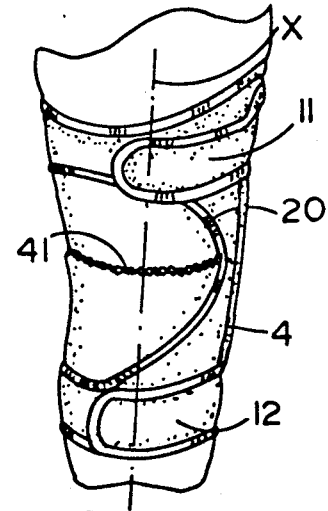
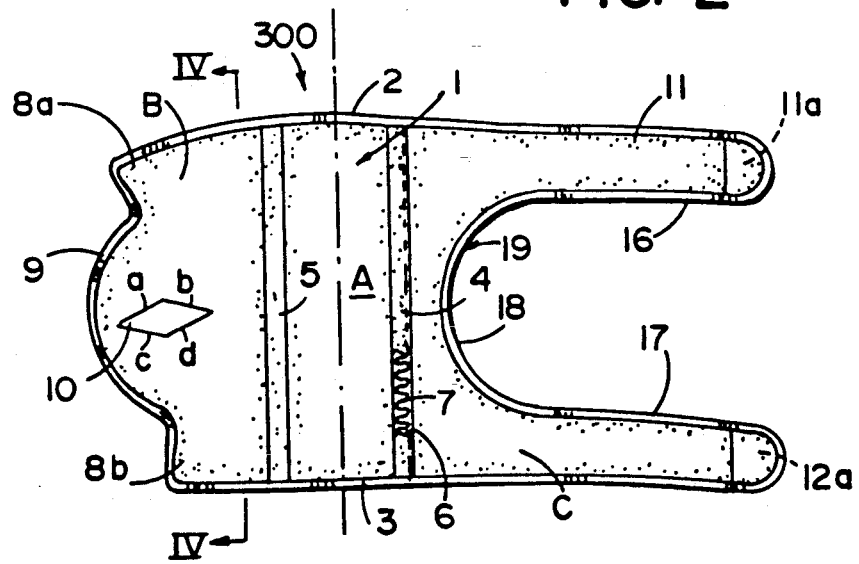
FIG. 1
FIG. 4
FIG. 2
FIG. 3

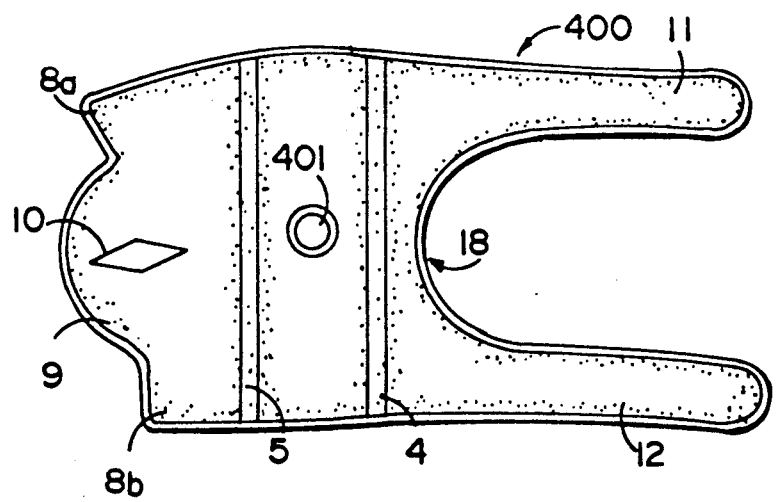
FIG. 5
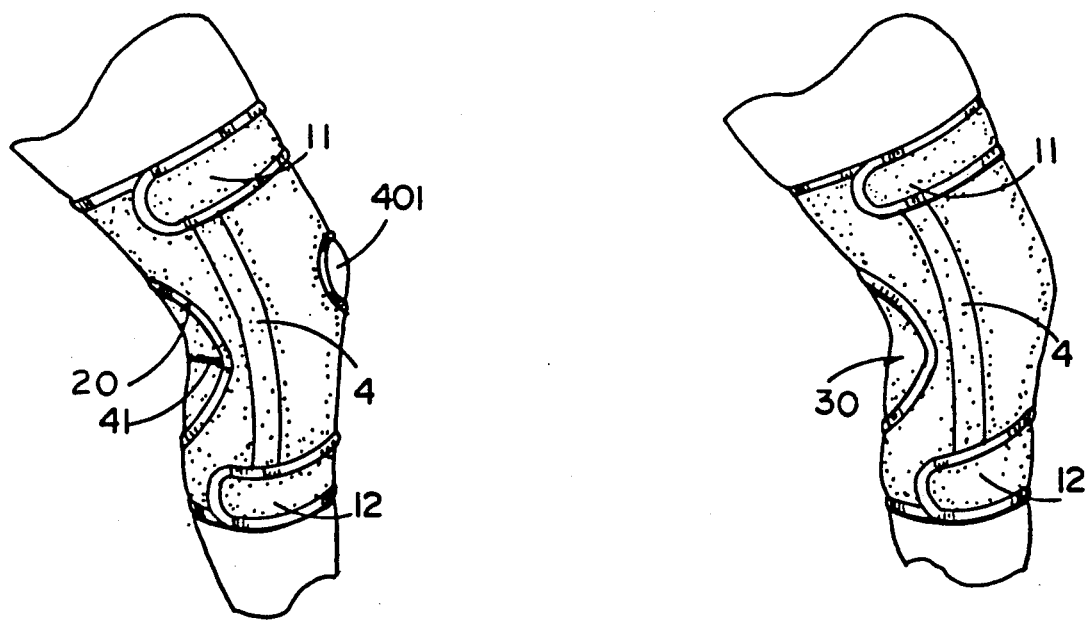
FIG. 6
FIG. 7

KNEE SLEEVE

BACKGROUND OF THE INVENTION

This invention relates to knee supports and, in particular, to a support adapted to prevent injuries to the knee and/or provide support for an already injured or weakened knee and is capable of stabilizing the knee without impairing circulation and normal flexibility.

The human knee is subjected to a wide variety of compressive, bending, twisting and lateral forces, particularly, when the individual is active in physically strenuous activities. Injuries to the knee are quite common among athletes and the general public. The most common occurring injuries relate to stretching or tearing of the various knee ligaments, injury to the cartilage and particular surfaces of the knee joint, and fractures. These type injuries are quite troublesome, because of the mechanical characteristics of the human limb joint. Furthermore, the repetitive, abnormal lateral excursions which cause abnormal shearing forces, frequently lead to early, accelerated and progressive degenerative changes in the bones of the joint.

Individuals who have sustained knee injuries, who have had operations to remove cartilage, or who have weak knee joints from causes such as arthritis primarily need protection against lateral motion of the knee in a direction transverse in the plane of flexion and extension, such as might be caused by a blow to the side of the knee. At the same time, a suitable knee support should not interfere with the normal flexion and extension of the leg. The support should protect the knee against sideways motions during both flexion and extension. As the healing process of a knee injury progresses, it has been difficult to provide support and bracing which is adjustable to meet the condition of a wearer from the initial several days of when the joint is most swollen, to the following days when swelling decreases gradually, and, later, over the ensuing weeks when gradually less bracing and support of the knee is required.

A frequently employed approach to support a weakened knee has been to apply adhesive tape around the joint in order to provide some measure of protection and added strength. This approach is expensive since it requires the time of a trainer, requires someone with knowledge of how to properly wrap the adhesive tape, and uses a significant amount of tape which is not reusable. Also, it leads to discomfort arising from impaired circulation and during the removal of the tape from the skin.

Other supports include various elastic sleeves, some using stiffeners to provide additional strength to the support in an effort to assist the wearer. Many of such sleeves are uncomfortable to wear because of seams which exert pressure on the popliteal area, i.e., the back side of the knee.

Other prior art devices include knee supports and braces characterized by hinges on the lateral and medial side of the knee, some have been characterized by straps, and some have employed belts or have utilized spiral wrappings extending above and below the kneecap.

SUMMARY OF THE INVENTION

In accordance with the present invention there is provided a unitary pull-on knee support having a generally cylindrical body comprising a flexible resilient sheath adapted to anatomically conform to the body member. The sleeve includes an arcuate back seam which arcs away from the popliteal area behind the knee. This makes it possible to provide a seamed rather than continuously woven sleeve without having to have an irritating seam running along the tender area behind the knee.

Other objects and many of the attendant advantages of this invention will be readily appreciated as the same become better understood by reference to the following detailed description when considered in connection with the accompany-drawings wherein:

BRIEF DESCRIPTION OF THE DRAWINGS

FIG. 1 is a side elevational view of the knee support of this invention;

FIG. 2 is a rear elevational view of the knee support of FIG. 1;

FIG. 3 is a plan view of the pattern from which the knee support of FIGS. 1-2 is formed;

FIG. 4 is a cross-sectional view taken along the plane IV—IV of FIG. 3.

FIG. 5 is a modification of the pattern of FIG. 3 in which an opening is provided for receiving the patella of a knee;

FIG. 6 is a side elevational view of the modified knee support of FIG. 5;

FIG. 7 is a side elevational view of still another modified knee support.

DESCRIPTION OF THE PREFERRED EMBODIMENTS

Figure 8:
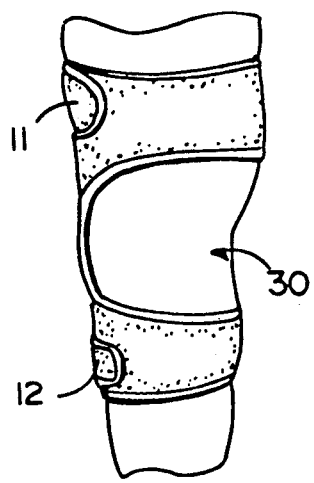
FIG. 8 is a rear elevational view of the knee support of FIG. 7.

In the preferred embodiments, the knee sleeve support 100 (FIG. 1) is provided with integral encircling straps 11 and 12 having hook fasteners 11a and 12a affixed to their outer ends. Openings are provided at both the thigh (top) and calf (bottom) ends of the support to accommodate the variance between thigh and calf circumference since an individual's thigh and calf circumference are rarely proportional.

A patella opening 401 (FIG. 5) can be provided when limited edema is present, with closed patella embodiments being utilized when edema control is paramount. An opening 30 (FIG. 7) to eliminate pressure in the sensitive popliteal area may or may not be provided. If not provided, a rear "C" seam 5 (FIG. 6) offset from the center of the popliteal area is provided to reduce pressure and inhibit material bunching in the popliteal area. The support is also provided with medial and lateral stays 7 (FIG. 3), which are preferably semi-rigid, flexible flat spiral coil metal stays but can be of any shape or formed from any material, such as plastics, which have been commonly used for this purpose. The knee supports are available in right and left styles to assure lateral closure for prevention of opposite leg medial irritation.

In use, the support 100 is pulled on the leg up over the knee to a position where the knee is approximately centered between the medial and lateral stays 7. In this position, either the "C" seam 5 is located off-center from the popliteal area or an opening 30 is provided in the popliteal area so as to eliminate any discomfort and rubbing generally experienced by seams which normally extend between the upper and lower edges of the sleeve 100 in the center of the popliteal area. In the embodiments of the supports, which include a patella opening 401, the opening is positioned with the patella protruding through the opening. Once the sleeve 100 is properly located, the upper and lower encircling straps 11 and 12 are wrapped about the thigh and calf, respectively. The lengths of the encircling straps 11 and 12 are preferably sufficient to encompass the thigh and calf at least once, and the free ends 11a and 12a of the legs 11 and 12 are attached either to the outer surface 31 of the body or the outer surface 31 of the encircling strap 11 or 12, as the case may be. As the encircling straps 11 and 12 extend over the medial and lateral stays 7, a substantially equally distributed, effective compression and firm stabilization of the stays is achieved to provide the required knee stability. It will be appreciated that compression may be adjusted to a desired level by increasing or decreasing the tightness of the encircling legs 11 and 12.

The knee sleeve support of the invention is formed from a resilient flexible material comprising an exposed outer surface or layer and an inner layer or surface adapted to be worn next to the body area. More particularly, the supports of this invention can be formed from substantially any natural or synthetic material, including both inelastic and elastic materials, having sufficient flexibility and resiliency to enable the support to anatomically conform to the body member to which it is applied. In addition, the supports include mutually intercooperating connector means comprising loop keeper means on at least a portion of the outer surface of the support and a companionate array of hook keeper means on at least a portion of the inner surface of the support which confront the loop keeper means when both keeper means are in an overlying relationship on the supports; the hook means being adapted in response to pressure against the loop means to intermesh with the loop means and releasably cling to the loop means, to be separated therefrom in response to a peeling quick yanking force.

The resilient flexible natural or synthetic materials suitable for use in the practice of the invention include fabrics made from inelastic fibers such as nylon fibers, polyester fibers, cotton fibers and the like; elastomers such as natural rubber, neoprene rubber and the like; and elasticized fibers comprising a blend of at least one inelastic fiber, such as nylon, polyester, cotton and the like and at least one elastomeric fiber, such as those sold under the trademark Lycra, and including combinations of two or more natural and/or synthetic materials, generally in the form of a laminated structure.

The preferred material comprises a flexible resilient elasticized fabric laminate comprising an outer elasticized fabric layer, an open-cell polymeric foam core and an inner or proximal elasticized fabric layer. The foam core is coextensive with and adhered to both inner and outer layers. The laminate is stretchable in all directions. The inner and outer layers comprise elasticized fabrics having substantially the same degree of stretch in all directions. The outer elasticized fabric layer is preferably a high moisture absorbent fabric comprising a blend of at least one inelastic fiber and at least one elastic fiber, with a blend of inelastic polyamide and elastic polyurethane being currently preferred. The outer surface has a brushed felt-like texture comprising myriad upstanding and relatively free fiber loop fastening means. The inner layer is preferably a lower moisture absorbent but good wicking fabric comprising an elasticized cotton fabric comprising a blend of cotton and at least one elastic fiber, preferably an elastic polyurethane fiber. The polymeric foam core is an open-celled cellular material which is preferably a polyurethane or polystyrene foam and is most preferably a polyethylene foam. Currently, a preferred composite comprises 35 weight percent polyamide, 42 weight percent cotton, 18 weight percent polyurethane elastic fiber and 5 weight percent open-cell polyethylene foam, based on total weight of the composite. The provision of elasticized fibers and fabrics from different natural and synthetic fibers is well-known in the art, and there is no need for elaboration. The composite is lightweight, stretchable to anatomically conform to the body member, durable and easily laundered in home washing machines. Drip-drying is the preferred method of drying laundered supports. The high-absorbent elasticized outer layer, the open-cell polymeric foam core and the low-absorbent elasticized inner layer cooperatively provide a breathable composite which aids in the transfer of moisture, such as perspiration from the wearer's body to the outer surface of the outer or exposed layer, which has sufficient porosity to enable moisture to be wicked from the body to the outer surface of the support. The elasticized cotton inner layer ensures dryness, provides a comfortable feel against the body and a feeling of soothing warmth for injured and arthritic joints when engaging in strenuous activities while minimizing heat buildup during such activities.

Referring to the drawings, the construction of one embodiment of the pull-on knee support in accordance with the invention is disclosed in FIGS. 1-7. The support, generally indicated as 100, is laid out in a planar manner in FIG. 3 exemplifying the pattern 300 of the material from which the support 100 is manufactured. Referring to FIG. 3, pattern 300 comprises an irregularly shaped elasticized fabric laminate 1 which, as shown in FIG. 4, includes an outer layer 31 comprising elasticized fabric having a brushed texture provided with myriad looped fasteners, a thin (0.1–0.3 inches) polymeric open-cell foamed cushion 32 and an inner layer 33 comprising an elasticized cotton fabric, all layers being coextensive with each other. Fabric laminate 1 is bound around its entire periphery by a sewn elastic binding 34.

The elasticized fabric of layer 31 comprises a blend of at least one inelastic fiber and at least one elastomeric fiber. Polyamides are currently the preferred inelastic fiber, with elastomeric polyurethane fibers, such as those available under the trademark Lycra being currently preferred. Foam cushion 32 is preferably polyethylene polystyrene or polyurethane open-cell foam, with polyethylene foam being currently preferred. Inner layer 33 comprises a blend of cotton and at least one of the elastomeric fibers already mentioned. A currently preferred construction comprises 35 weight percent polyamide, 42 weight percent cotton, 18 weight percent elastomeric polyurethane and 5 weight percent polyethylene foam, based on total weight of fabric laminate.

The material of pattern 300 comprising elasticized fabric laminate 1 is shown with outer surface 31 appearing to the viewer. Pattern 300 is of an irregular configuration comprising a central region A merging into respective end portions B and C, such regions defining a top edge 2 and bottom edge 3. Central region A is provided with lateral reinforcing strip 4 and medial reinforcing strip 5, each of which are vertically disposed and are intended to lie along and on each side of the approximate vertical center line of the wearer's leg (FIGS. 5 and 6). Reinforcing strips 4 and 5 each comprise a sewn-in pocket 6 having contained therein a flexible stay 7, preferably a flexible flattened metal spiral coil, but can be any shape and formed from any other material, such as plastics, which have been commonly used for this purpose. The construction of the reinforcing strips are identical, thus, only strip 5 is described in detail.

Bottom edge 3 is substantially straight along its entire length, including the end regions B and C portions. Top edge 2 is provided with a convex curvature extending along its entire length from beginning to end, thus making it somewhat longer than edge 3. This discrepancy in length between edges 2 and 3 is designed to provide support 100 with a larger diameter upper opening 21 because of the larger circumference, generally of the thigh in comparison to the upper calf. As a result, support 100 will exhibit a modest taper-in from top to bottom (see FIG. 1).

End region B is provided with an end edge defining an arcuate shaped portion or protuberance 9 and closure tabs 8a and 8b extending from the ends of the arc forming the arcuate protuberance 9. Closure tabs 8a and 8b extend from the end points of edges 2 and 3 and merge into ends of the arc formed by C-shaped protuberance 9. End region B is also provided with a flattened rhombic cutout 10, which is intended to substantially collapse into a line joint which becomes seam 41 (FIGS. 1 and 5) of support 100 during the sewing together of pattern 300.

Side region C is provided with elongated encircling straps 11 and 12, respectively, extending away from central region A and having hook pads on inner layer 33 at ends 11a and 12a, respectively. The length of encircling straps 11 and 12 are each preferably of sufficient length to encircle the entire thigh or calf, as the case may be, at least once, most preferably about 1½ times, so as to double back on themselves. The inner edges 16 and 17, respectively, of encircling straps 11 and 12, respectively, merge into an end edge 18 having an arcuate portion or recess 19. The arcuate C-shaped end edge portion 18 is shaped and dimensioned to receive convex arcuate protuberance 9, thus forming a substantially smooth close fit which, when edge portions 9 and 19 are attached by sewing or otherwise, becomes the C-shaped seam 5 of support 100 (FIGS. 1 and 5).

Before forming support 100, elastic binding 34 is sewn or stitched around the periphery of pattern 300. Pattern 300 is then placed around an appropriate mandrel, and arcuate edge portion or protuberance 9 is attached to edge portion 19 by stitching or otherwise forming seam 5. The mating of edge portions 18 and 9 to form the arcuate or C-shaped seam 5 of sleeve 100 locates seam 5 offset from the center of the popliteal area behind the knee. The collapse of cutout 10 defined by sides a, b, c and d of cutout 10 into a line joint is stitched to form straight seam 41 extending laterally a small distance across the popliteal area of support 100 (FIGS. 1 and 5). Tabs 8a and 8b, which extend from the respective ends of the arc of edge portion 9 and 18, respectively, to top edge 2 and bottom edge 3, respectively, are stitched only with elastic binding 34, thus these tabs 7 and 8 are free to provide for adjusting to variations in lower thigh and/or upper calf girth to ensure a proper fit of support 100 at the thigh and/or calf.

While support 100, as described, is adapted for use on the left knee, it will be appreciated that a support 100 for use on the right knee is made in a similar way from similar patterns with the end portions B and C being reversed.

In use, support 100 is pulled onto the leg and positioned at the knee area, with the knee or patella being located midway between the top and bottom edges 1 and 2 and substantially midway between medial and lateral supports 4 and 5, which become vertically positioned between and along the center line of the leg. It will be appreciated that, when the support is properly positioned, tabs 8a and 8b will define an opening substantially at the rear of the leg above and below the popliteal area. Tab 8a will be then held to provide a tight fit at the rear of the knee while encircling strap 11 is stretched towards the front of the leg across medial reinforcing strip 5 and over the front of the leg. Strap 11 is then drawn along the side of the leg across lateral reinforcing strip 4 and fastened to looped surface 31, preferably at or by hooks 11a on the inner surface of the proximal encircling strap. In the most preferred embodiment, strap 11 is of sufficient length that it can be wrapped around the thigh area at least 1½ times and fastened on the front or lateral side of the leg to the looped surface 31 of strap 11. This not only provides substantially equal support compression and stabilization to both medial and lateral sides of the knee, but also reduces discomfort, such as chafing, on the medial side of the knee and in the popliteal area.

Closure tab 8b is held in a like manner as distal strap 12 is then drawn across medial reinforcing strap 5 and lateral reinforcing strap 4 and attached to looped surface 31, preferably of the distal belt, by hooks 12a on the inner surface of the distal encircling strap. In the most preferred embodiment, distal strap 12 is of sufficient length that it can be wrapped around the upper calf area at least 1½ times and fastened on the front or lateral side of the leg to the looped surface 31 of strap 12. As with strap 11, this not only provides substantially equal support, compression and stabilization to both medial and lateral sides of the knee, but also reduces discomfort, such as chafing, on the medial side of the knee and in the popliteal area. The application of the support to the right knee follows the same procedure as for the left knee.

FIG. 5 discloses pattern 400 which is different than pattern 300 in that it is shaped to provide a patella opening 401, located midway between the top and bottom edges 2 and 3, respectively, of central area A. Patella opening 401 is located approximately midway between lateral supports or reinforcing strips 4 and 5, respectively, of central area A of pattern 400. All other features of pattern 400 are otherwise identical to their like features of pattern 300. The exposed edges of patella opening 401 are also provided with elastic binding 34.

Figure 9:
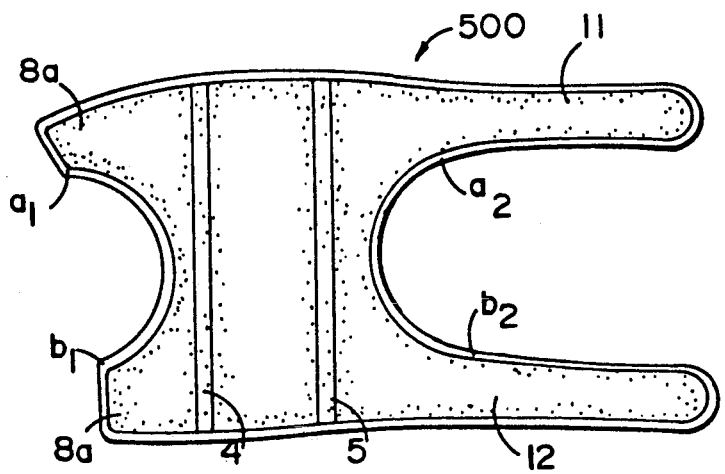
FIG. 9 is a pattern of the material used in forming the knee support of FIG. 7.
Figure 10:
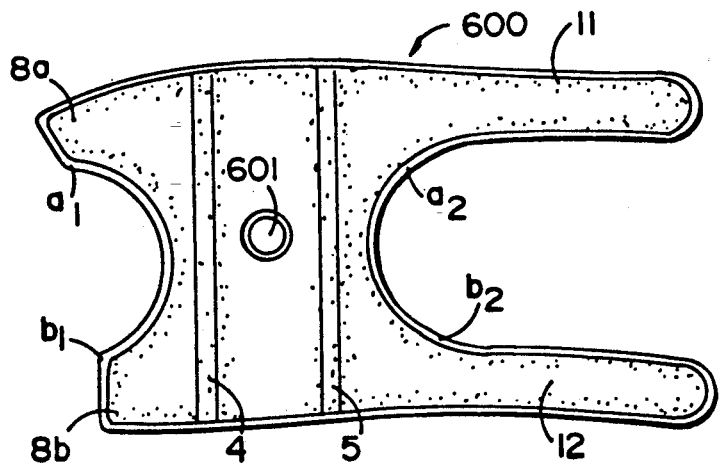
FIG. 10 is a modification of the pattern of FIG. 9 in which an opening is provided for receiving the patella of a knee.
Figure 11:
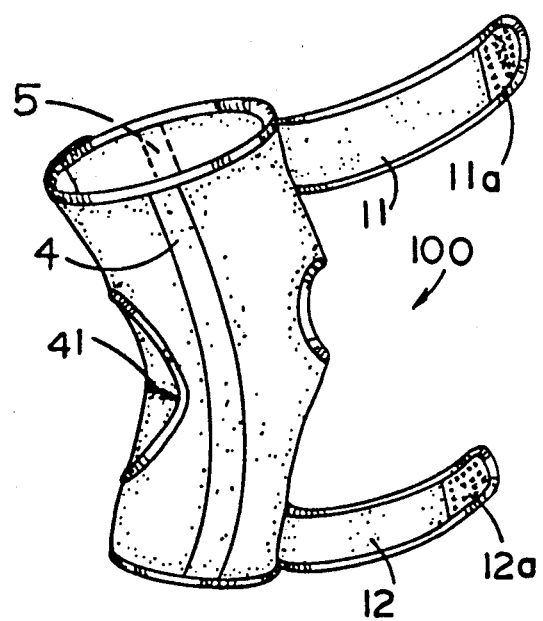
FIG. 11 shows the sleeve of claim 10 before it has been applied to a user's leg and before the compression straps have been secured.

FIGS. 9 and 10 disclose still another modified support 200 formed from the pattern 500 (FIG. 9) which includes all of the elements of pattern 300 with one exception. Instead of a convex arcuate end edge or protuberance 9, pattern 500 includes a concave arcuate or C-shaped edge pattern 501 formed into end region B. Edge portion 501 is substantially a mirror image of edge portion 18 of region C. In forming support 200 from pattern 500, edge portions 18 and 501 are mated at their respective ends ($a_1$ to $a_2$ and $b_1$ to $b_2$) and are stitched at those points to form a substantially circular popliteal opening 30 (see FIG. 7). This opening 30 thus substantially eliminates any annoying stitching in the popliteal area.

FIG. 10 discloses still another pattern 600 which is identical to pattern 500, except that pattern 600 includes patella opening 601, having the same location on pattern 601 and the same purpose as patella opening 401 on pattern 400.

Support 200 of FIGS. 9 and 10 is used in substantially the same way as described in relation to support 100 of FIGS. 1-7 and 8. The only difference is in the opening 30 located in the popliteal area behind the knee which is substituted for C-shaped seam 5 of support 100, all as described above. Both C-shaped seam 5 and the popliteal opening 30 serve the same purpose of substantially eliminating the commonly used stitching seam which extends vertically between the top edges of the sleeve making the sleeve uncomfortable and causing a rubbing action that irritates the popliteal area behind the knee. In addition, both embodiments 100 and 200 have all the other advantages over prior knee supports, all as set forth above.

While several embodiments of this invention have been disclosed with particularlity above, numerous other modifications of the same within the scope of the invention will be readily apparent to those skilled in the art. Thus, it is considered that various configurational modifications of the knee sleeve of this invention will occur to those skilled in the art and are considered also to be encompassed by this invention. Further, the scope of the invention of this knee sleeve, which is suitable for the treatment and prevention of injuries to the knee area, is to be limited solely by the claims appended hereto.

The embodiments of the invention in which an exclusive property or privilege is claimed are defined as follows:

1. A knee support comprising a sleeve adapted to be placed over the knee;

said sleeve being configured to substantially anatomically conform to the knee, lower thigh and upper calf;

said sleeve including an upper edge and a lower edge defining openings at the top and bottom, respectively, for receiving the knee, lower thigh and upper calf;

said sleeve being formed of a piece of flexible resilient material having a top edge and a bottom edge, which form the said upper and lower edges of said top and bottom openings, respectively, and two opposite end edge portions which are attached together to form the sleeve; and said end edge portions having substantially identical arcuate shaped portions having arcs directed in the same direction creating an arcuate seam when attached to each other whereby said sleeve can be placed on said knee with the portion of the material between said end edges fitted over the front or knee cap portion of the knee and the arcuate seam located offset from the popliteal area behind the knee.

2. A knee support comprising a sleeve adapted to be placed over the knee;

said sleeve being configured to substantially anatomically conform to the knee, lower thigh and upper calf;

said sleeve including an upper edge and a lower edge defining openings at the top and bottom, respectively, for receiving the knee, lower thigh and upper calf;

said sleeve being formed of a piece of flexible and elasticized material having a top edge and a bottom edge, which form the said upper and lower edges of said top and bottom openings, respectively, and two opposite end edge portions which are attached together to form the sleeve; and said end edge portions having substantially identical arcuate shaped portions having arcs directed in the same direction creating an arcuate seam when attached to each other whereby said sleeve can be placed on said knee with the portion of the material between said end edges fitted over the front or knee cap portion of the knee and the arcuate seam located offset from the popliteal area behind the knee.

3. A knee support comprising a sleeve adapted to be placed over the knee;

said sleeve being configured to substantially anatomically conform to the knee, lower thigh and upper calf;

said sleeve including an upper edge and a lower edge defining openings at the top and bottom, respectively, for receiving the knee, lower thigh and upper calf;

said sleeve being formed of a piece of flexible and elasticized material having a top edge and a bottom edge, which form the said upper and lower edges of said top and bottom openings, respectively, and two opposite end edge portions;

said two opposite end edge portions having arcuate shaped portions, one of said end edge portions defining at least two elongated flexible and elasticized straps extending from a base area generally adjacent said arcuate shaped portion of said one edge, one of said straps being integral with said one end edge and with said top edge and the other of said straps being integral with said one edge and with said bottom edge; said two elongated straps extending substantially parallel to each other for wrapping around the lower thigh and upper calf;

means for attaching said straps to another part of said sleeve; and the other of said end edge portions being seamed to approximately said base area to form said sleeve.

4. A knee support of claim 3 in which the straps are sufficiently long to encircle the lower thigh and upper calf.

5. A knee support of claim 3, wherein the end edge portion opposite said one end edge portion defining said integral straps includes a tab adjacent each end of the arc forming said arcuate shaped portion of said opposite end edge.

6. A knee support of claim 3 in which the arcs of said arcuate shaped portions of said end edges are directed in the same direction, said arcuate shaped portions being attached to each other to form an arcuate seam whereby said sleeve can be placed on said knee with the portion of the material between said end edges fitted over the front or knee cap portion of the knee and the arcuate seam located offset from the popliteal area behind the knee.

7. A knee support of claim 3 in which the arcs of said arcuate shaped portions of said end edges are directed in opposite directions; and said arcuate shaped portions being attached to each other at the terminal ends of the arcs forming said arcuate shaped portions whereby an opening is provided in said sleeve to provide an opening in the popliteal area behind the knee.

8. A knee support, comprising: a sleeve adapted to be placed over the knee;

said sleeve being configured to substantially anatomically conform to the knee, lower thigh and upper calf;

said sleeve including an upper edge and a lower edge defining openings at the top and bottom, respectively, for receiving the knee, lower thigh and upper calf;

said sleeve being formed of a piece of flexible and elasticized material having a top edge and a bottom edge, which form said upper and lower edges of said top and bottom openings, respectively, and two opposite end edge portions;

said two opposite end edge portions having arcuate shaped portions defining arcs directed in opposite directions, one of said two opposite end edge portions defining at least two elongated flexible and elasticized straps extending from a base area generally adjacent said arcuate shaped portion of said one end edge portions, one of said straps being integral with said one end edge portions of said sleeve and with said top edge, and the other of said straps being integral with said one end edge portions and with said bottom edge; said two elongated straps extending substantially parallel to each other to encircle the lower thigh and upper calf;

said arcuate shaped portions being attached to each other at the terminal ends of the arcs forming said arcuate shaped portions whereby an opening is provided in said sleeve to provide an opening in the popliteal area behind the knee; and the other of said end edge portions being seamed to approximately said base areas to form said sleeve.

9. A knee support of claim 3 in which the sleeve and integral straps are constructed of the same material having inside and outside surfaces, said outside surface including a looped fastening material; and said inside surface of the ends of said strap including hooked fastening material interlockable with said looped fastening material.

10. A knee support of claim 3 in which elongated reinforcing strips are mounted on said material between said end edges, said strips extending in a longitudinal direction between said upper and lower edges and located so as to be positioned on the medial and lateral sides of the knee of a wearer.

* * * * *

UNITED STATES PATENT AND TRADEMARK OFFICE
CERTIFICATE OF CORRECTION

PATENT NO. : 5,139,477

DATED : August 18, 1992

INVENTOR(S) : Helena Peters

It is certified that error appears in the above-identified patent and that said Letters Patent is hereby corrected as shown below:

Column 2, line 12;
  "accompany drawings" should be --accompanying drawings--.
Column 2, line 57;
  "seam 5" should be --seam 20--.
Column 2, line 61;
  Delete "stays 7" and insert therefor --reinforcing strips 4 and 5--.
Column 2, line 62;
  "coil metal stays" should be --metal coil stays 7--.
Column 3, line 3;
  Delete "stays 7" and insert therefor --reinforcing strips 4 and 5--.
Column 3, line 4;
  "seam 5" should be --seam 20--.
Column 3, line 21;
  Delete "stays 7" and insert therefor --reinforcing strips 4 and 5--.
Column 5, line 17;
  "strip 5" should be --strip 4--.
Column 5, line 56;
  "seam 5" should be --seam 20--.
Column 5, line 62;
  "seam 5" should be --seam 20--.
Column 5, line 63;
  "seam 5" should be --seam 20--.
Column 5, line 64;
  "seam 5" should be --seam 20--.

UNITED STATES PATENT AND TRADEMARK OFFICE
CERTIFICATE OF CORRECTION

PATENT NO. : 5,139,477

DATED : August 18, 1992

INVENTOR(S) : Helena Peters

It is certified that error appears in the above-identified patent and that said Letters Patent is hereby corrected as shown below:

```
Column 7, line 20;
    "seam 5" should be --seam 20--.
Column 7, line 21;
    "seam 5" should be --seam 20--.
```

Signed and Sealed this

Eleventh Day of January, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,139,477
DATED      : August 18, 1992
INVENTOR(S): Helena Peters

It is certified that error appears in the above-indentified patent and that said Letters Patent is hereby corrected as shown below:

Column 6, line 5:

"these tabs 7 and 8" and insert --tabs 8a and 8b--.

Signed and Sealed this

Nineteenth Day of April, 1994

Attest:

BRUCE LEHMAN

*Attesting Officer*     *Commissioner of Patents and Trademarks*